(12) United States Patent
Jörgensen

(10) Patent No.: US 8,137,630 B2
(45) Date of Patent: Mar. 20, 2012

(54) LIGHT-EMITTING SMELL-ALTERING AROMA DISPENSER

(75) Inventor: Carsten Jörgensen, Kastanienbaum (CH)

(73) Assignee: Ming Jen Hsiao, Miaoli (TW)

( * ) Notice: Subject to any disclaimer, the term of this patent is extended or adjusted under 35 U.S.C. 154(b) by 376 days.

(21) Appl. No.: 12/422,249

(22) Filed: Apr. 11, 2009

(65) Prior Publication Data

US 2010/0260646 A1    Oct. 14, 2010

(51) Int. Cl.
```
A62B 7/08      (2006.01)
A61H 33/12     (2006.01)
D06F 75/00     (2006.01)
F17C 7/04      (2006.01)
B67D 7/80      (2010.01)
B67D 7/08      (2010.01)
G04C 23/00     (2006.01)
B05B 1/24      (2006.01)
B05C 1/00      (2006.01)
A62C 13/62     (2006.01)
A62C 13/66     (2006.01)
A62C 31/00     (2006.01)
```
(52) U.S. Cl. ........ 422/123; 422/120; 422/125; 392/406; 392/405; 222/146.5; 222/639; 239/71; 239/136; 239/303

(58) Field of Classification Search .............. 222/146.5, 222/639; 239/71, 136, 303; 392/405, 406; 422/120, 123, 125
See application file for complete search history.

(56) References Cited

U.S. PATENT DOCUMENTS

| | | | |
|---|---|---|---|
| 3,873,806 A * | 3/1975 | Schossow | 392/402 |
| 2002/0176704 A1* | 11/2002 | Roe | 392/393 |
| 2008/0130266 A1* | 6/2008 | DeWitt et al. | 362/96 |
| 2009/0136390 A1* | 5/2009 | Yang | 422/125 |
| 2010/0025490 A1* | 2/2010 | Bushman et al. | 239/7 |
| 2011/0110072 A1* | 5/2011 | Hsiao | 362/96 |
| 2011/0110118 A1* | 5/2011 | Hsiao | 362/643 |
| 2011/0110119 A1* | 5/2011 | Hsiao | 362/643 |
| 2011/0110824 A1* | 5/2011 | Hsiao | 422/125 |

FOREIGN PATENT DOCUMENTS

GB    2469505 A  * 10/2010

* cited by examiner

*Primary Examiner* — Walter D Griffin
*Assistant Examiner* — Christopher Vandeusen
(74) *Attorney, Agent, or Firm* — Chun-Ming Shih

(57) ABSTRACT

A light-emitting smell-altering aroma dispenser includes a casing having a bottom opening blocked by a base member, heater members supported on trays above a control circuit board in the casing, tubular aroma containers inserted through the top wall of the casing into the heater members at the trays and holding a respective aromatic substance for heating by the heater members to release a pleasant smell subject to the control of the control circuit board, and light emitting devices controlled by the control circuit board to emit light toward the aroma containers when the aroma substance in the aroma containers is being heated to release a pleasant smell.

17 Claims, 17 Drawing Sheets

LIGHT-EMITTING SMELL-ALTERING AROMA DISPENSER

BACKGROUND OF THE INVENTION

1. Field of the Invention

The present invention relates to aroma dispensers and more particularly, to a light-emitting smell-altering aroma dispenser that produces a lighting effect when releasing one or a combination of different pleasant smells to create a warm atmosphere.

2. Description of the Related Art

An aroma diffuser is known having a number of wooden sticks placed in the diffuser body thereof for absorbing an essential oil. By means of the volatile characteristic of the essential oil, the incense dispenser releases a pleasant smell into the air. However, the essential oil changes into vapor at a low speed. Further, this kind of aroma diffuser cannot produce a mixed smell or any lighting effect.

There is known a fan-operated aroma dispenser for wall mounting. This design of fan-operated aroma dispenser utilizes a fan to causes currents of air in spreading the smell of an aromatic substance. The fan consumes electric energy and causes a noise during operation. Further, this design of fan-operated aroma dispenser cannot create a warm atmosphere or produce a mixed smell or any lighting effect.

There is also known a candleholder type aroma dispenser that utilizes a candle to heat a water tray that carries a certain amount of water and few drops of an essential oil in the water. This design of candleholder type aroma dispenser is not safe in use. During the use of the candleholder type aroma dispenser, the fluid may be forced by an external force to splash over the surroundings accidentally.

There is known a lamp-based aroma dispenser that utilizes a lamp to heat an aromatic substance, causing the aromatic substance to release a pleasant smell. This design of lamp-aroma dispenser is still not satisfactory in function because it takes a long time to cause the aromatic substance release a pleasant small and cannot produce a mixed smell or a lighting effect.

Further, the aforesaid various different types of aroma dispensers are simply used to release a pleasant smell, they cannot attract people's eyes.

SUMMARY OF THE INVENTION

The present invention has been accomplished under the circumstances in view. It is one object of the present invention to provide a light-emitting smell-altering aroma dispenser, which utilizes tubular aroma containers to hold different liquid aromatic substances for releasing different pleasant smells either at a same time or separately, avoiding oil falling accident and assuring a high level of safety.

To achieve this and other objects of the present invention, a light-emitting smell-altering aroma dispenser comprises a casing, a plurality of heater members, a plurality of trays, a base member, a control circuit board and a plurality of aroma containers. The casing is a hollow member. Each tray has a light emitting device installed therein. The control circuit board controls the heater members to heat the aroma containers separately or at one same time. The aroma containers are tubular members that admit light. The aroma containers are respectively inserted through respective through holes on the top wall of the casing and the axial center through hole of each of the heater members and supported on the trays. Each aroma container is kept in close contact with the periphery of the axial center through hole of the associating heater member. The aroma containers can be heated separately at different time periods or at one same time. Different colors of aromatic substances may be placed in the aroma containers for releasing different pleasant smells.

The sense of smell of a person will become dull or less acute when smelling one same smell for a long period of time. By means of heating different aromatic substances in different aroma containers to release different smells, the invention keeps your sense of smell smart.

Further, the control circuit board can control multiple heater members to heat different aromatic substances in different aroma containers at the same time, thereby releasing a mixed smell like the preparation of cocktail.

The light-emitting smell-altering aroma dispenser further comprises a plurality of light emitting devices respectively installed in the trays and/or the control circuit board. When electrically connected, the light emitting devices emit light toward the aroma containers, thereby producing a lighting effect. The light emitting devices can be color LEDs (light emitting diodes). The aromatic substances can be prepared in different colors. Therefore, when the light emitting devices light up the aroma containers as the aromatic substances are being heated to release pleasant smells, a romantic, warm and graceful atmosphere is created.

Further, the aroma containers can be prepared from transparent or semi-transparent glass, acrylic, ceramic, crystal, or perforated metal sheet material.

Further, the aromatic substances can be essential oil, scented candle, flower essence and fragrance.

Preferably, the aromatic substances are prepared in a predetermined color.

Further, each heater member can be prepared from mica, PTC (positive temperature coefficient technology) resistor or cement resistor.

The tubular aroma containers are detachably installed in the casing for easy replacement. A consumer can selectively set tubular aroma containers with different aromatic substances in the casing for releasing different pleasant smells. Therefore, the design of the present invention attracts consumers to buy.

When compared to conventional designs that release one specific smell slowly, the invention can release different pleasant smells and produce a lighting effect to create a romantic, warm and graceful atmosphere. Further, the aroma containers are tubular containers held in the respective through holes of the casing and supported on the respective trays. Therefore, the light-emitting aroma dispenser is safe in use, and the aromatic substances will not fall out of the aroma containers during the use of the light-emitting aroma dispenser.

Further, the light-emitting smell-altering aroma dispenser can be made comprising a casing, at least one heater member, at least one tray, a base member, a control circuit board, and at least one aroma container. For example, the light-emitting smell-altering aroma dispenser can be made having only one tubular aroma container. Further, a light emitting device is installed in the tray and controllable to emit light toward the tubular aroma container. Therefore, the light-emitting smell-altering aroma dispenser produces a lighting effect when releasing a good smell. Further, the heater member and the tray hold the aroma container stably in place, avoiding falling of the aromatic substance out of the aroma container.

Further, a user can purchase a series of aroma containers that have different aromatic substances contained therein, and selectively set one or a number of the series of aroma containers in the light-emitting smell-altering aroma dispenser for heating by the associating heater member(s) to release the selected pleasant smell. Therefore, a user can change the aroma container to produce a different pleasant smell and a different color of light subject to one's feeling.

DETAILED DESCRIPTION OF THE PREFERRED EMBODIMENT

Figure 1:
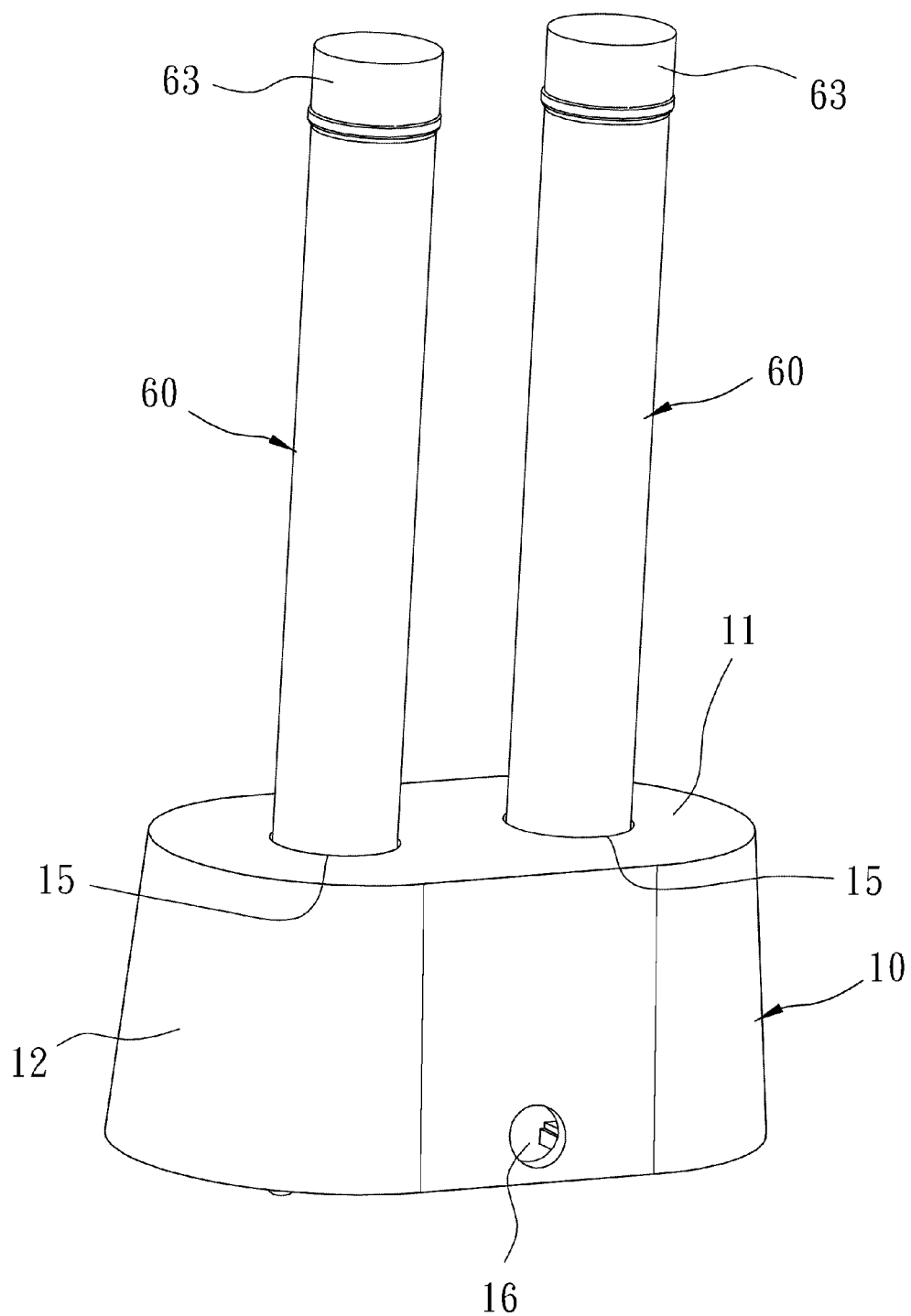
FIG. 1 is an elevational view of a light-emitting smell-altering aroma dispenser in accordance with a first embodiment of the present invention.
Figure 2:
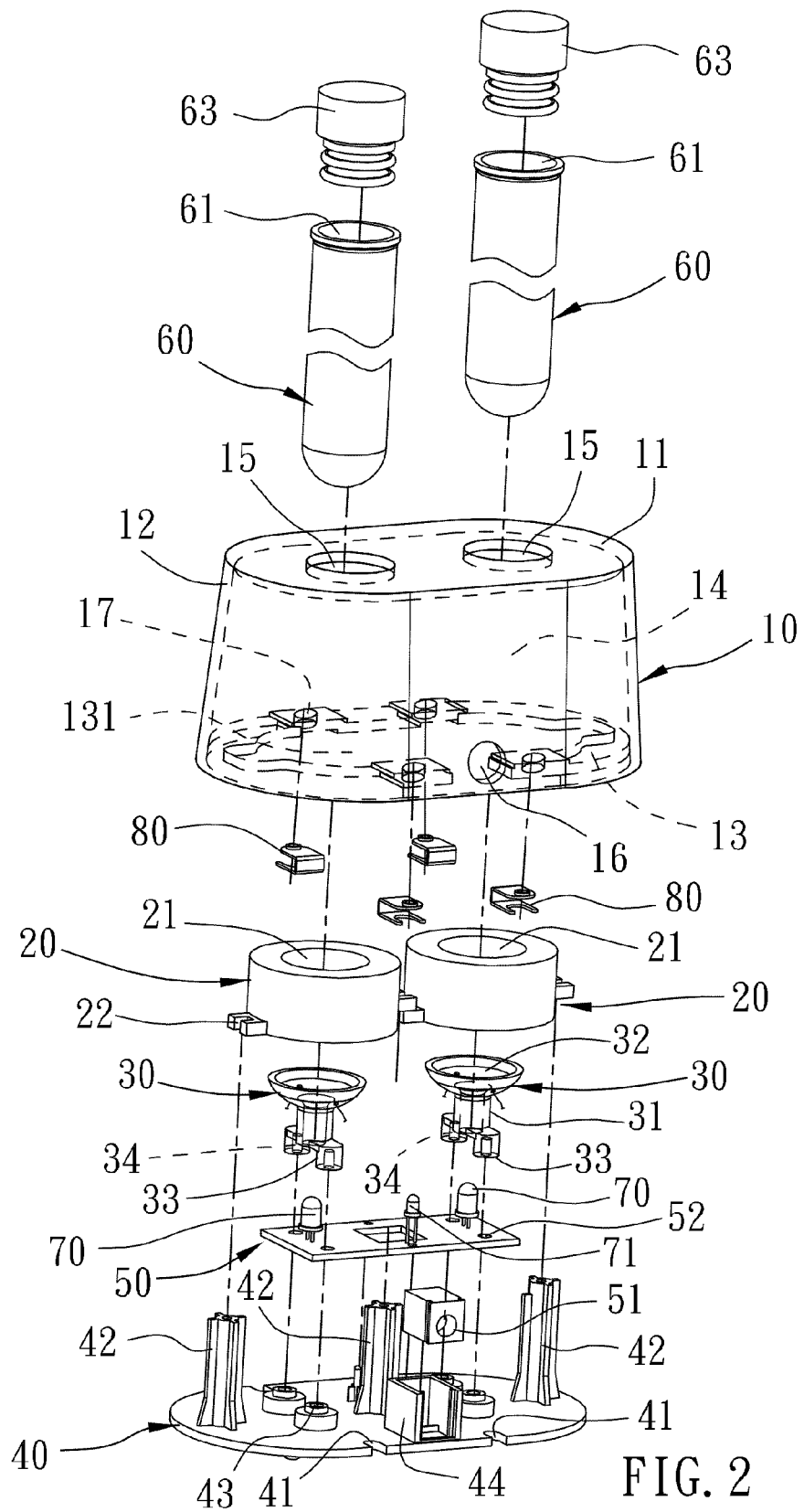
FIG. 2 is an exploded view of the light-emitting smell-altering aroma dispenser in accordance with the first embodiment of the present invention.
Figure 3:
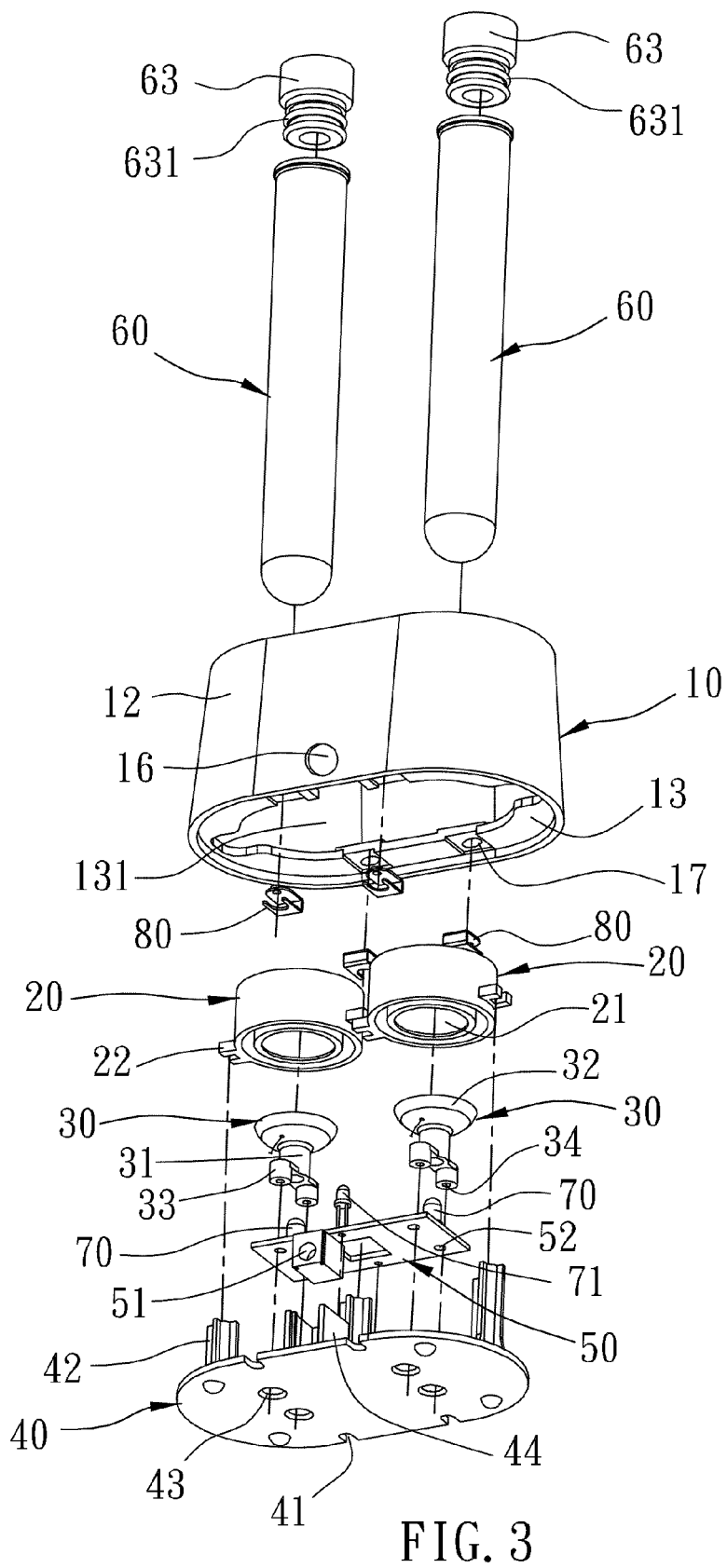
FIG. 3 is another exploded view of the light-emitting smell-altering aroma dispenser in accordance with the first embodiment of the present invention when viewed from another angle.

Referring to FIGS. 1-3, a light-emitting smell-altering aroma dispenser in accordance with a first embodiment of the present invention is shown comprising a casing 10, two heater members 20, two trays 30, a base member 40, a control circuit board 50, two aroma containers 60, a plurality of light emitting devices 70, and a plurality of clamping plates 80.

The casing 10 has a top wall 11, a peripheral wall 12, a bottom wall 13, an accommodation chamber 14, at least two through holes 15, a wire hole 16, and a plurality of locating holes 17. The through holes 15 are located on the top wall 11. The bottom wall 13 has an opening 131. The wire hole 16 is located on the peripheral wall 12 at one side.

The heater members 20 are cylindrical members mounted in the accommodation chamber 14 inside the casing 10 and respectively aimed at the through holes 15. Each heater member 20 has an axial center through hole 21, and a plurality of lugs 22 arranged at two opposite lateral sides. According to this embodiment, the two heater members 20 are joined together by means of affixing corresponding lugs 22 together. Further, each heater member 20 can be prepared from mica, PTC (positive temperature coefficient technology) resistor or cement resistor.

The trays 30 are respectively arranged at the bottom side of the heater members 20. Each tray 30 has a tray body 32, a tubular stem 31 located on the bottom side of the tray body 32, and two legs 33. The tray body 32 is shaped like a hollow, rounded dish. The legs 33 are symmetrically disposed at two sides of the tubular stem 31, each having a locating hole 34 at the center.

The base member 40 is joined to the bottom side of the casing 10 to close the opening 131. The base member 40 has a plurality of mounting notches 41, a plurality of columns 42, a plurality of mounting through holes 43, and a rack 44. The columns 42 are respectively fastened to the lugs 22 of the heater members 20, supporting the heater members 20 firmly in place.

The control circuit board 50 is adapted for controlling the power loop of the light-emitting smell-altering aroma dispenser and providing electricity to the heater members 20 in sequence or simultaneously to generate heat. The control circuit board 50 has a power jack 51 and a plurality of mounting through holes 52. The power jack 51 is positioned in the rack 44 of the base member 40 and aimed at the wire hole 16 of the casing 10 for the connection of an external power cord (not shown). The mounting through holes 52 are respectively fastened to the locating holes 34 of the trays 30 and the mounting through holes 43 of the base member 40 by fastening members (not shown).

The aroma containers 60 are light transmissive tubular members respectively inserted through the through holes 15 of the casing 10 and the axial center through holes 21 of the heater members 20 and supported on the trays 30. After installation of the aroma containers 60, the bottom end of each aroma container 60 is kept in close contact with the periphery of the axial center through hole 21 of the associating heater member 20.

Figure 13:
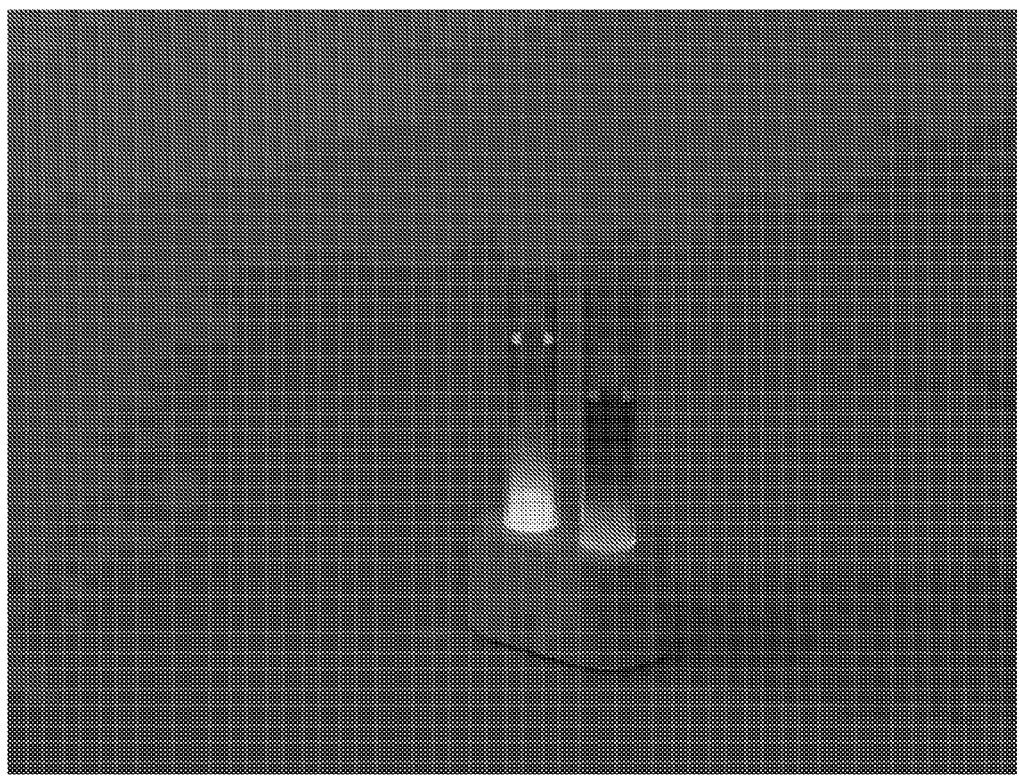
FIG. 13 shows a color picture of a status of use of a real product of two-aroma container type light-emitting smell-altering aroma dispenser according to the present invention.

The light emitting devices 70 are respectively mounted in the tubular stems 31 of the trays 30. When electrically connected, the light emitting devices 70 emit light toward the aroma containers 60 to light up the aromatic substances A and B in the aroma containers 60 at night, producing a lighting effect and creating a romantic, warm and graceful atmosphere. When the control circuit board 50 controls one heater member 20 to heat the respective aroma container 60, the respective light emitting device 70 is turned on to light up the respective aroma container 60, enabling the user to know which aroma container 60 is being heated. On the contrary, when the control circuit board 50 stops one heater member 20 from heating the associating aroma container 60, the associating light emitting device 70 is turned off. FIG. 13 is a color picture of a status of use of the light-emitting smell-altering aroma dispenser.

The clamping plates 80 are respectively affixed to the locating holes 17 of the casing 10. When the base member 40 is fastened to the casing 10 to close the opening 16, the mounting notches 41 are respectively fastened to the clamping plates 80 by fastening members (not shown).

Figure 4:
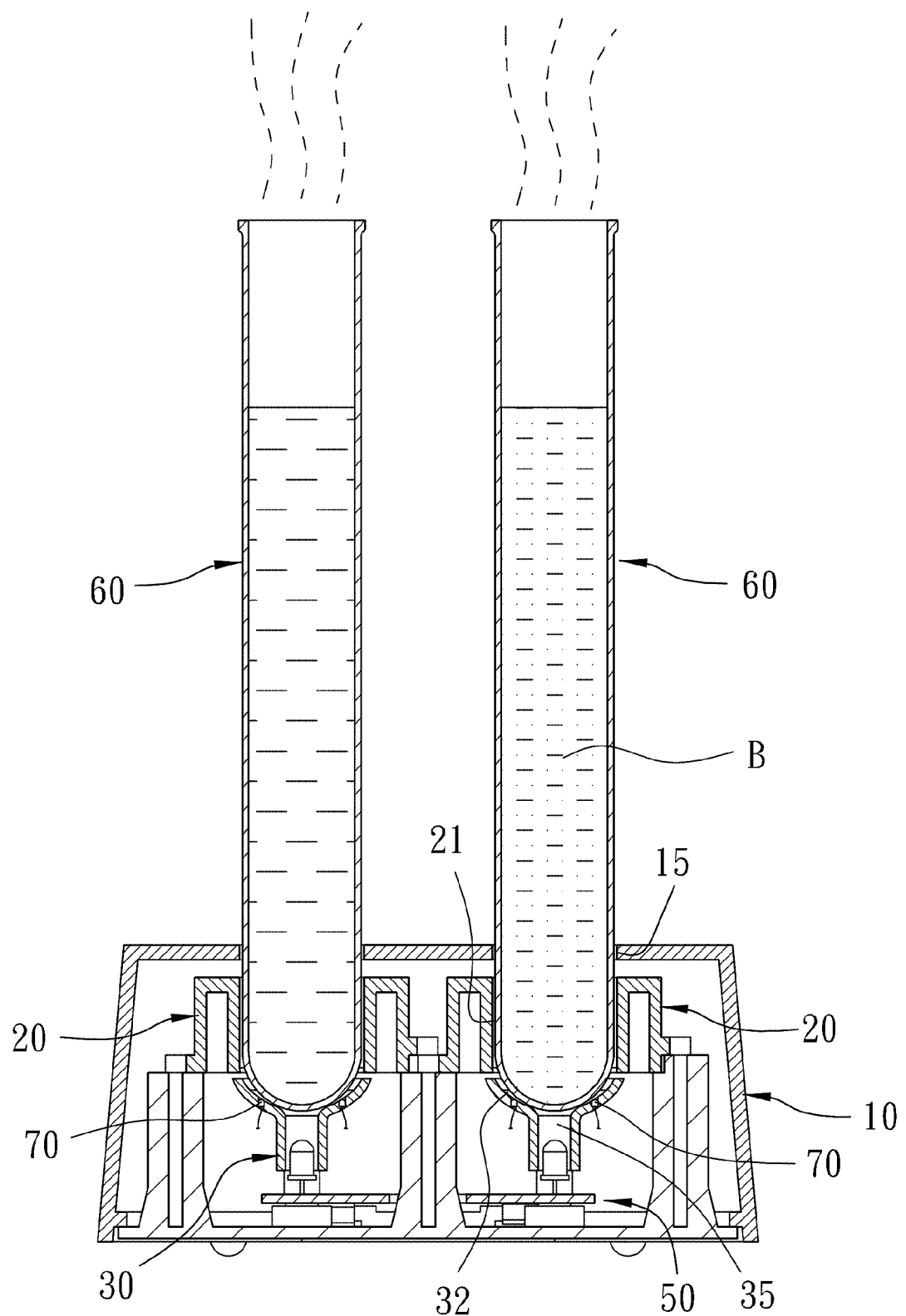
FIG. 4 is a sectional assembly view of the light-emitting smell-altering aroma dispenser in accordance with the first embodiment of the present invention.

Referring to FIG. 4, the aroma containers 60 are respectively inserted into the through holes 15 of the casing 10 and held in place by the heater members 20 and the trays 30, avoiding overflow of the liquid aromatic substances A and B. Further, each aroma container 60 is kept abutted against the periphery of the axial center through hole 21 of the associating heater member 20. After putting aromatic substances A and B in the aroma containers 60, the user may set various operation modes of the control circuit board to control the operation of the two heater members 20 in heating the aromatic substances A and B in the aroma containers 60 for generating different pleasant smells at different time periods, or in heating the aromatic substances A and B in the aroma containers 60 at a same time for generating a mixed smell of the aromatic substances A and B. Further, by means of controlling the light emitting devices 70 to light up the colorful aromatic substances A and B in the aroma containers 60, the invention produces a lighting effect and creates a romantic, warm and graceful atmosphere. Further, each aroma container 60 is equipped with a plug 63. The plug 63 is a cylindrical member having ribs 631 extending around the periphery of the lower part thereof at different elevations for friction engagement with the inner diameter of the associating aroma container 60 to seal the top opening 61 of the associating aroma container 60, avoiding escape of the smell of the aromatic substance A or B.

When compared to known designs of incense burners that commonly utilize an integrated dish to hold a liquid incense at the top side of the burner body, the use of the tubular aroma containers 60 to hold liquid aromatic substances according to the present invention eliminates the problem of splashing of a liquid incense or aromatic substance. Further, the invention utilizes DC/AC power inversion for causing the heater members 20 to heat the aroma containers 60, assuring heating stability. Further, the heater members 20 can be controlled to heat the associating aroma containers 60 one after another at a predetermined time interval. Further, the control circuit board 50 cuts off power supply from the heater members 20 automatically when the set heating time is up, assuring high level of safety. The heating time is set subject to calculation of the amount of the aromatic substances put in the aroma containers 60. Therefore, the aromatic substances A and B can be fully used up when the set heating time is up.

Figure 5:
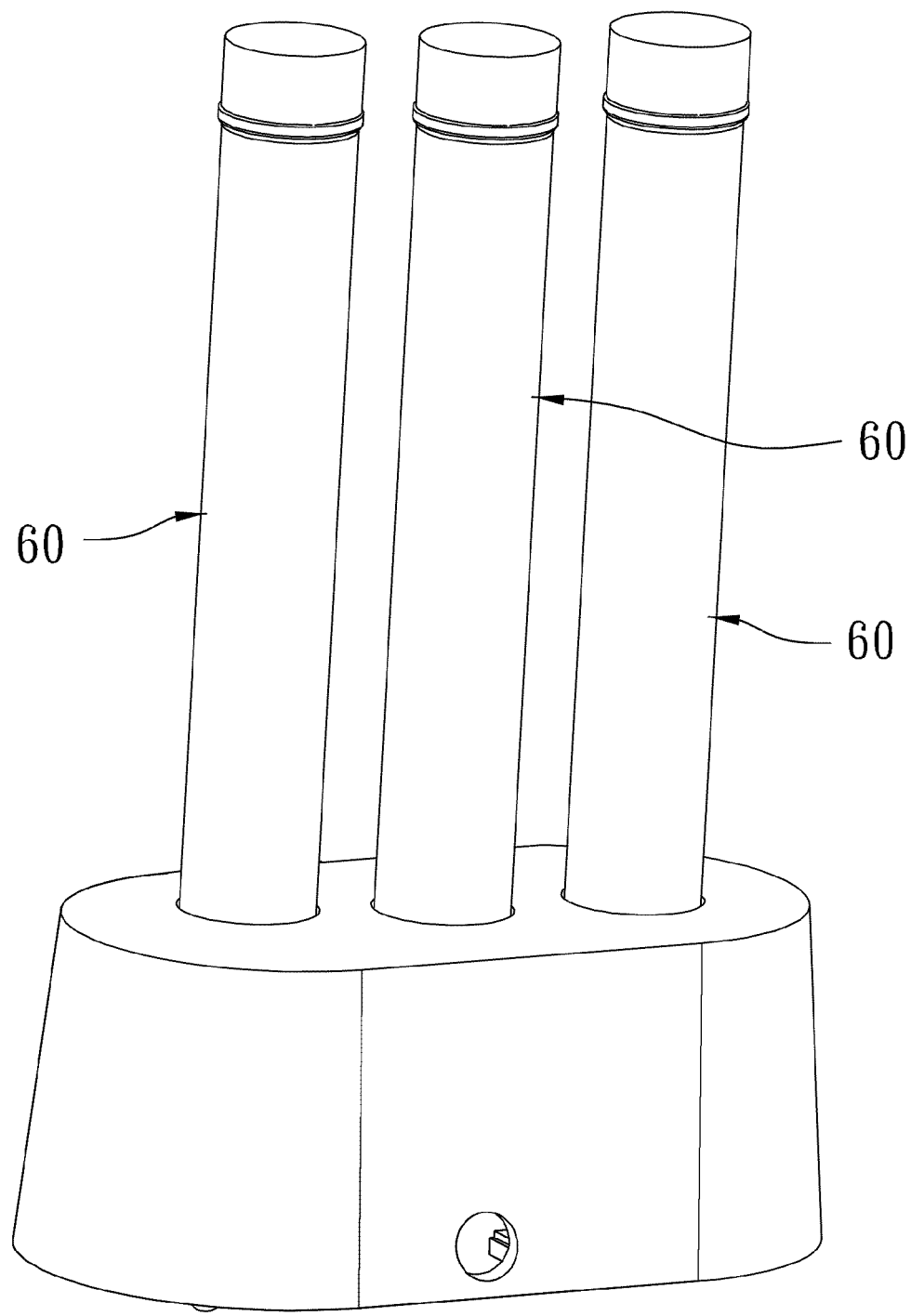
FIG. 5 is an elevational view of a light-emitting smell-altering aroma dispenser in accordance with a second embodiment of the present invention.
Figure 6:
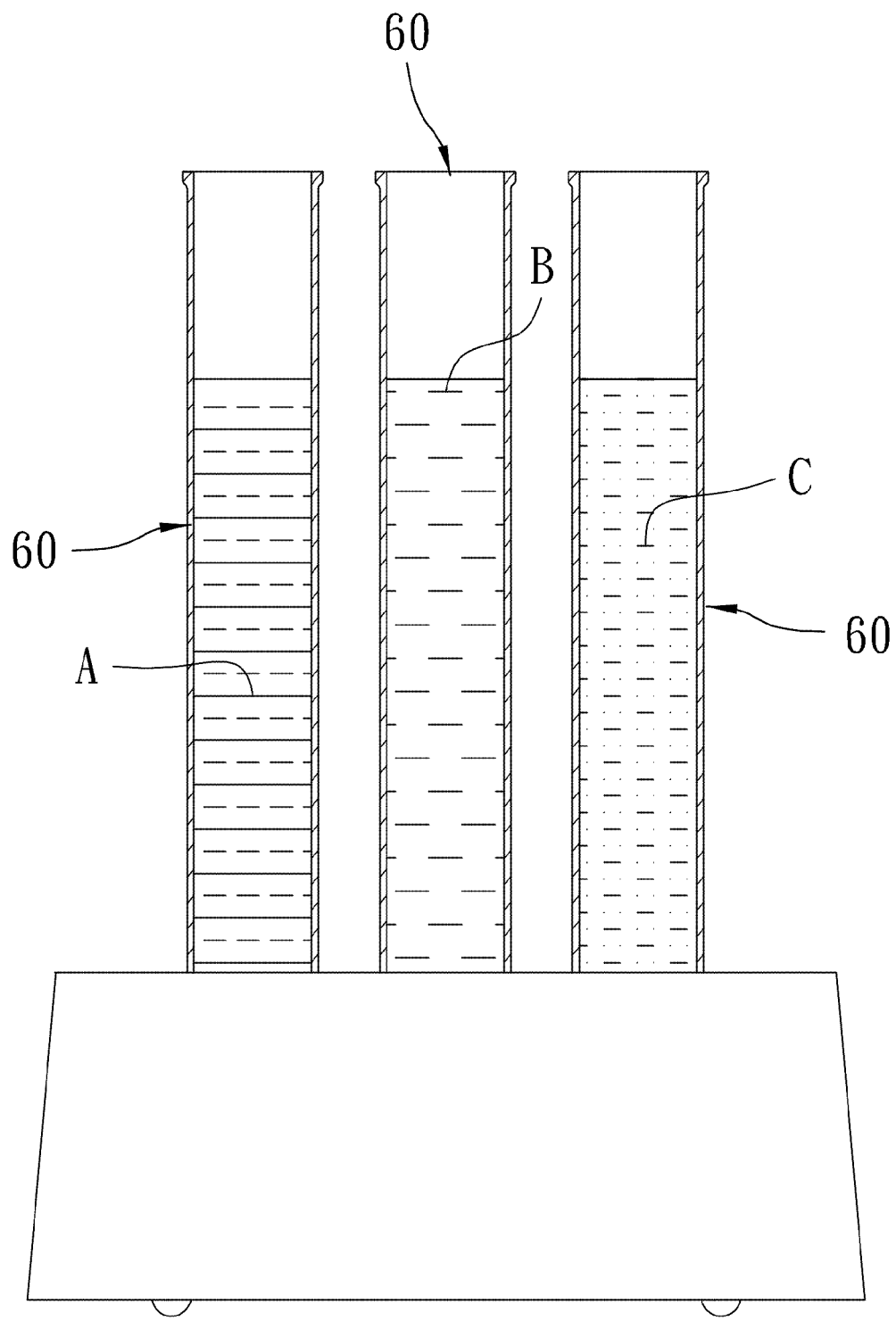
FIG. 6 is a schematic sectional view of the light-emitting smell-altering aroma dispenser in accordance with the second embodiment of the present invention.
Figure 14:
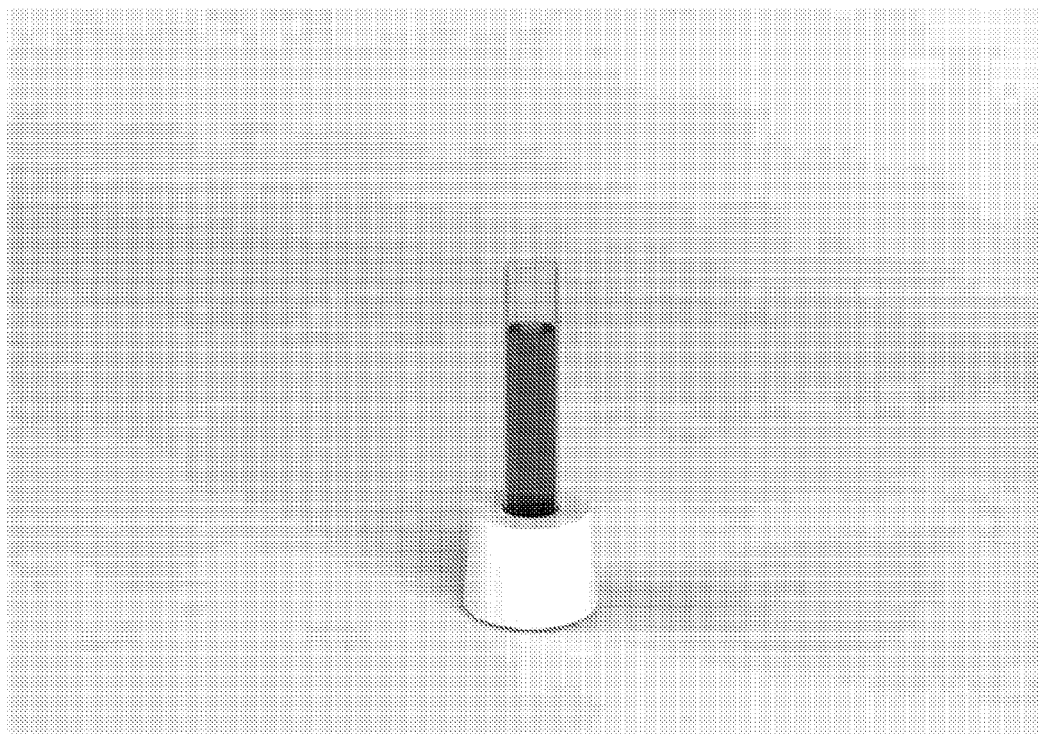
FIG. 14 shows a color picture of a status of use of a real product of single aroma container type light-emitting smell-altering aroma dispenser according to the present invention.
Figure 15:
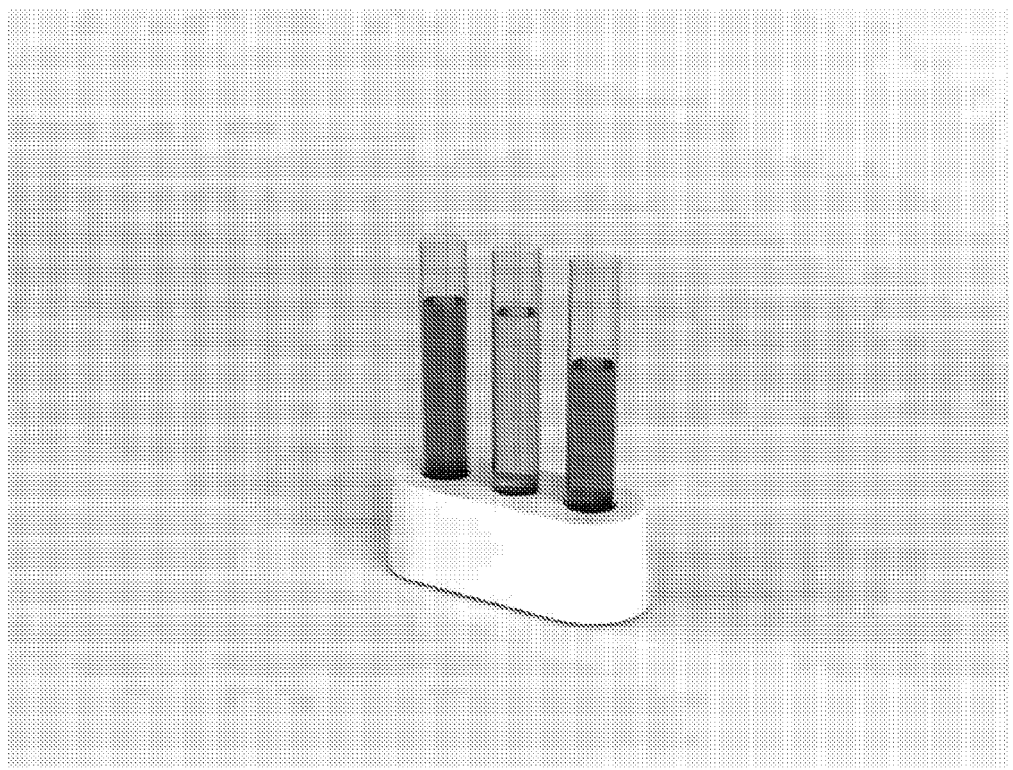
FIG. 15 shows a color picture of a status of use of a real product of three-aroma container type light-emitting smell-altering aroma dispenser according to the present invention.

FIGS. 5 and 6 show a light-emitting smell-altering aroma dispenser in accordance with a second embodiment of the present invention. This second embodiment is substantially similar to the aforesaid first embodiment with the exception that this second embodiment is equipped with three aroma containers 60 to hold three different colors of aromatic substances A, B and C that release different pleasant smells when heated. The use of this second embodiment is substantially similar to the aforesaid first embodiment. Therefore, no further detailed description in this regard is necessary. From FIG. 14, you can see the light-emitting smell-altering aroma dispenser with three different colors of aromatic substances.

Figure 7:
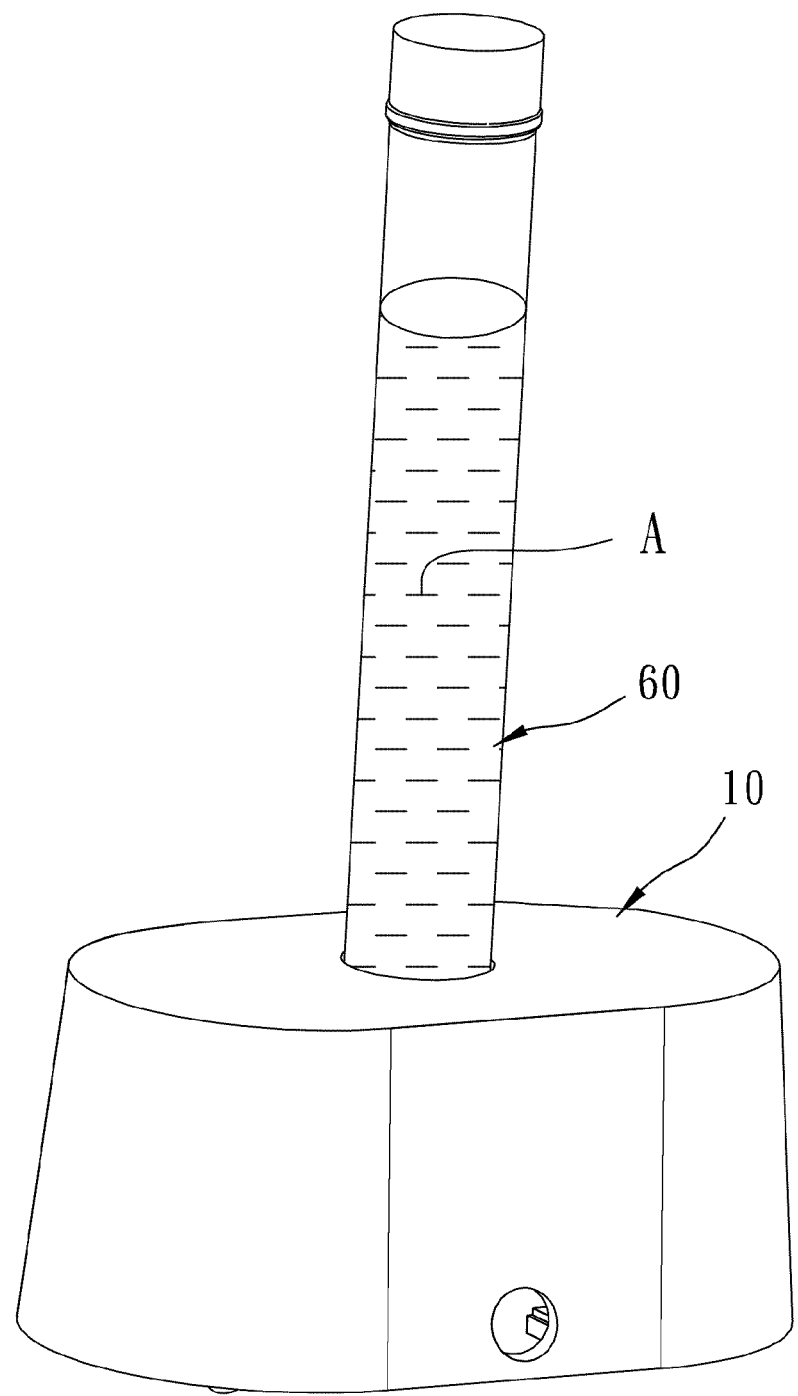
FIG. 7 is a schematic elevational view of a light-emitting smell-altering aroma dispenser in accordance with a third embodiment of the present invention.
Figure 8:
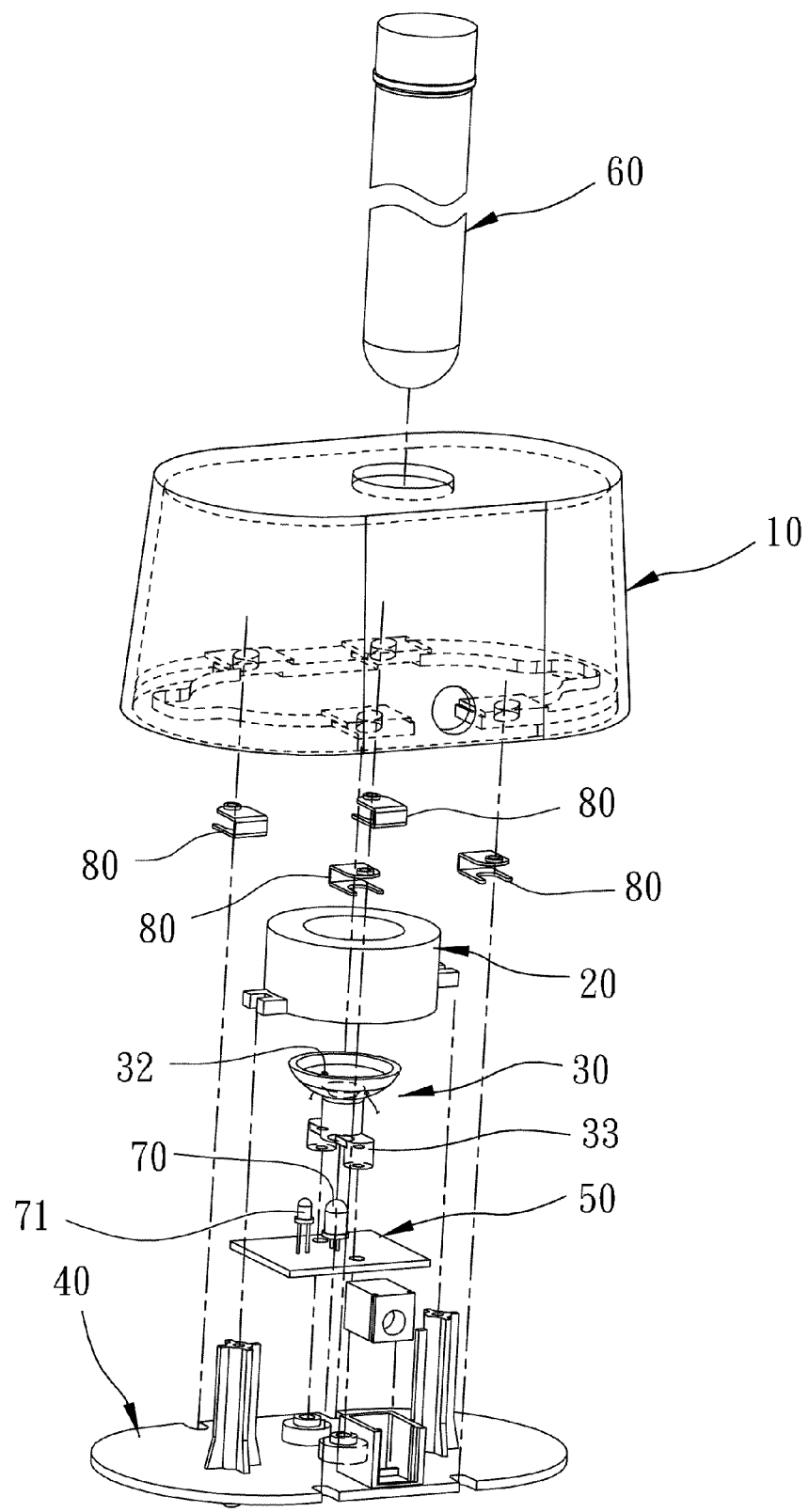
FIG. 8 is an exploded view of the light-emitting smell-altering aroma dispenser in accordance with the third embodiment of the present invention.
Figure 9:
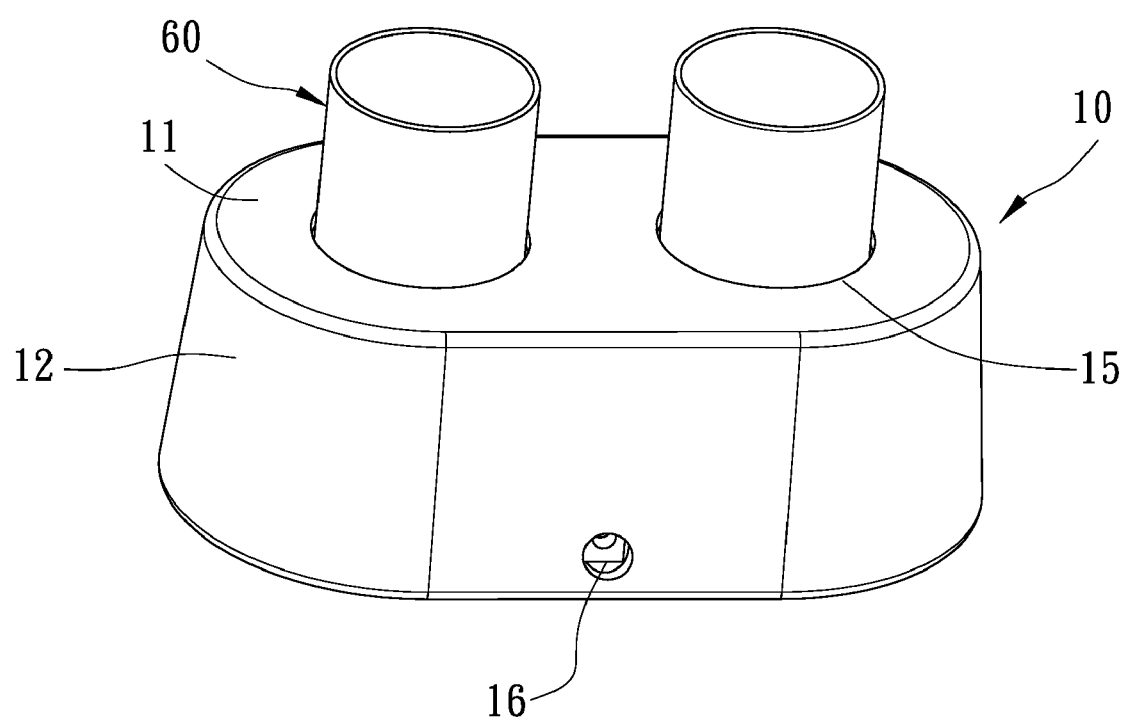
FIG. 9 is a schematic elevational view of a light-emitting smell-altering aroma dispenser in accordance with a fourth embodiment of the present invention.
Figure 10:
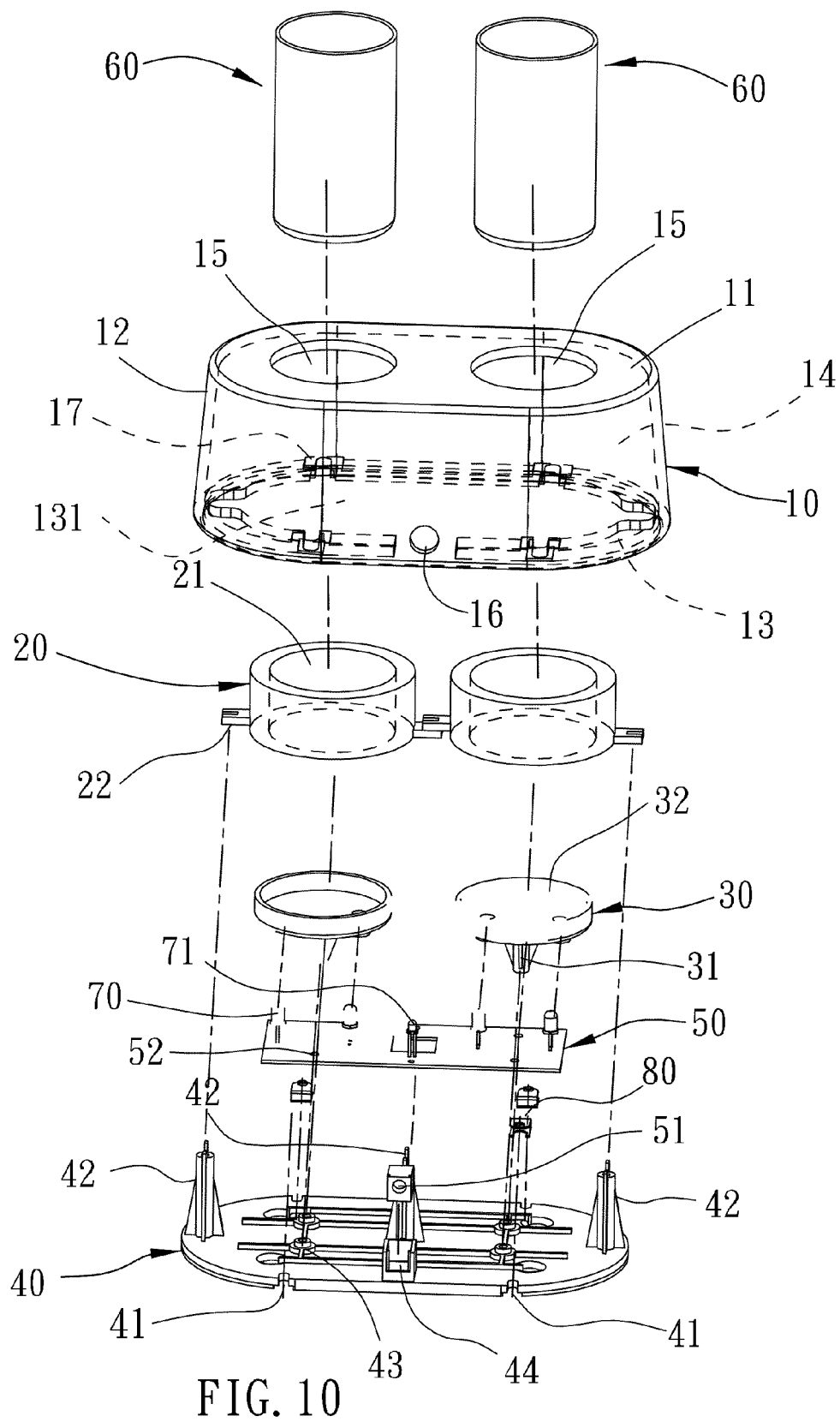
FIG. 10 is a perspective exploded view of the light-emitting smell-altering aroma dispenser in accordance with the fourth embodiment of the present invention.
Figure 11:
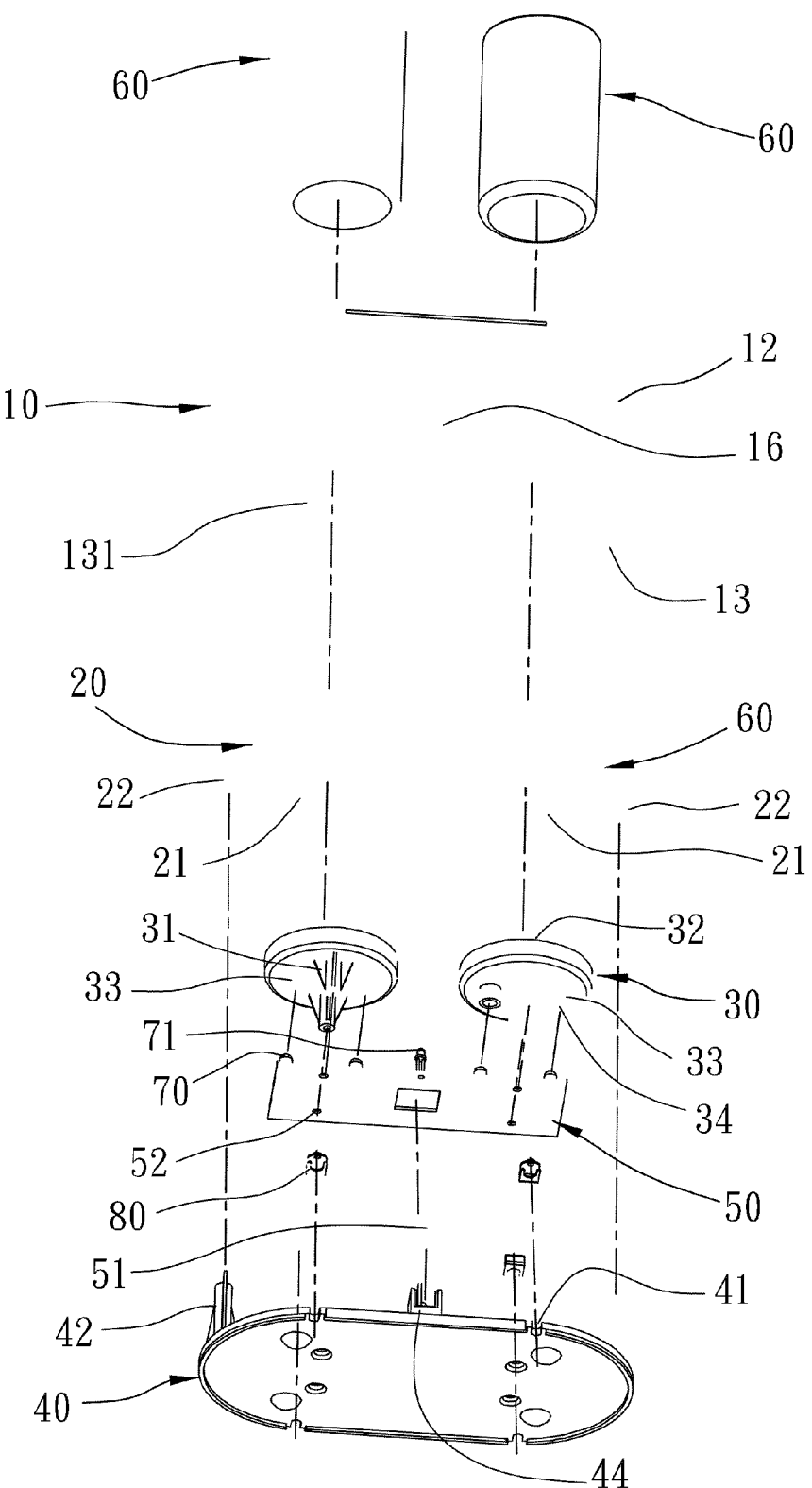
FIG. 11 is an exploded view of the light-emitting smell-altering aroma dispenser in accordance with the fourth embodiment of the present invention when viewed from another angle.
Figure 12:
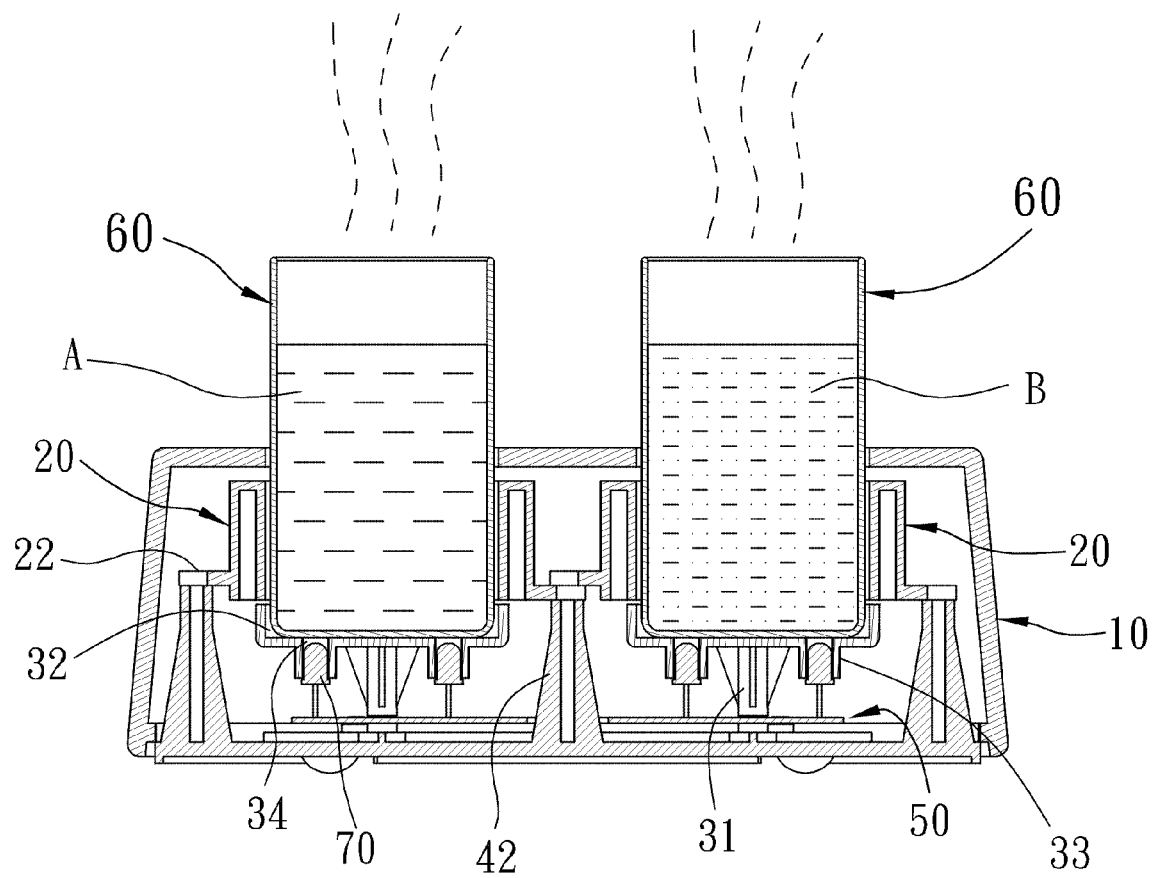
FIG. 12 is a schematic sectional view of the light-emitting smell-altering aroma dispenser in accordance with the fourth embodiment of the present invention.

FIGS. 7 and 8 show a light-emitting smell-altering aroma dispenser in accordance with a third embodiment of the present invention. The light-emitting smell-altering aroma dispenser in accordance with this third embodiment comprises a casing 10, a heater member 20, a tray 30, a base member 40, a control circuit board 50, an aroma container 60, a plurality of light emitting devices 70, and a plurality of clamping plates 80.

According to this third embodiment, the aroma container 60 is a tubular member holding an aromatic substance A, which is a color essential oil. The control circuit board 50 controls the heater member 20 to heat the aroma container 60, and cuts off power supply from the heater member 20 when a predetermined heating time is up. Preferably, the heating time is calculated subject to the amount of the aromatic substance A, assuring a high level of safety. Further, the lighting effect of this third embodiment is same as the aforesaid first and second embodiments.

According to any of the aforesaid three embodiments, the light-emitting smell-altering aroma dispenser provides a lighting effect when releasing a pleasant smell. Under the illumination of light, people can see the presence of the aromatic substance(s) when smelling a pleasant smell. Therefore, the invention makes people to feel warm and pleasant. Further, because the aroma container 60 is a tubular member positioned in the associating heater member 20 and supported on the associating tray 30, the contained liquid aromatic substance will splash over the floor accidentally.

Figure 16:
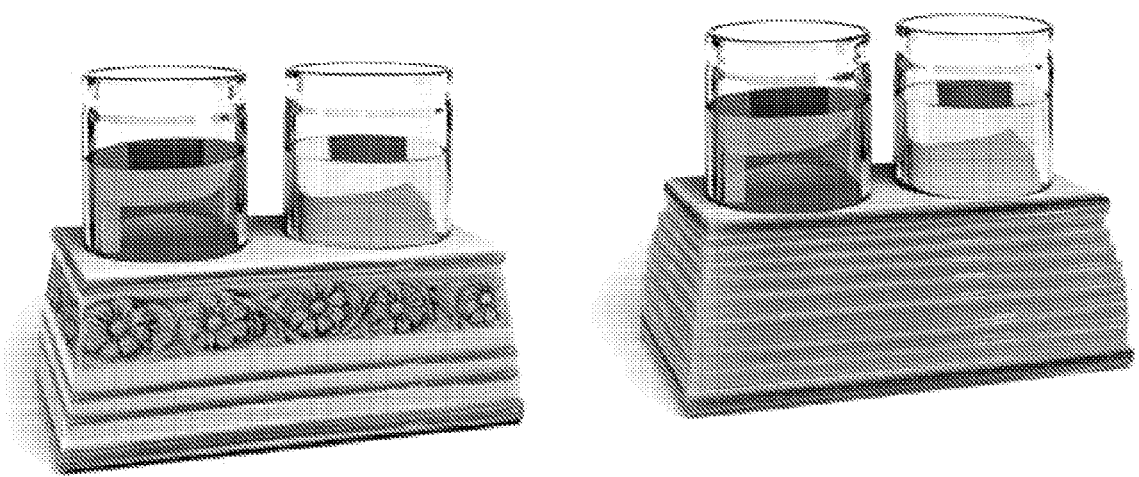
FIG. 16 shows a color picture of a status of use of a real product of cup-like aroma container according to the present invention.

FIGS. 9-12 show a light-emitting smell-altering aroma dispenser in accordance with a fourth embodiment of the present invention. According to this fourth embodiment, the aroma containers 60 are made in the form of a glass cup, and the trays 30 are made to match the cup-like aroma containers 60. Further, this fourth embodiment includes 5 light emitting devices 71, four installed in the tubular stems 31 of the trays 30 and one mounted on the control circuit board 50. This fourth embodiment is suitable for use in a big space, public place or outdoor open space to produce a big amount of pleasant sell and a striking color of light (see FIG. 16). The use of this fourth embodiment is same as the aforesaid various embodiments, and therefore not further detailed description in this regard is necessary.

Figure 17:
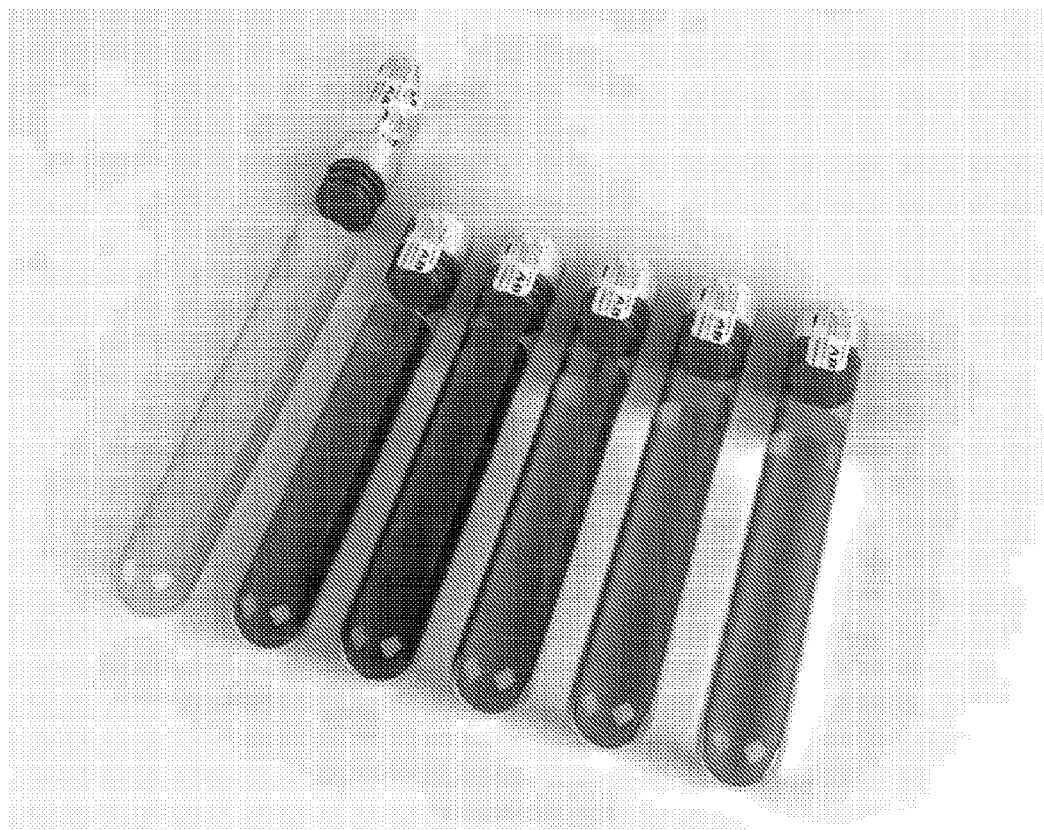
FIG. 17 shows a color picture of a real product of tubular aroma container according to the present invention.

Preferably (see FIG. 17), a user can purchase a series of aroma containers 60 that have different aromatic substances contained therein, and selectively set one or a number of the series of aroma containers 60 in the light-emitting smell-altering aroma dispenser for heating by the associating heater member(s) to release the selected pleasant smell. Therefore, a user can selectively alter the aroma container to produce a different pleasant smell and a different color of light subject to one's feeling.

Further, the control circuit board 40 has at least one light emitting device 71 installed therein to light up the inside space of the casing 10. Further, the casing 10 can be prepared from transparent or semi-transparent glass, acrylic, ceramic, crystal, or perforated metal sheet material. Under the illumination of the internal light emitting device 71, the casing 10 produces a warm lighting effect.

A prototype of light-emitting smell-altering aroma dispenser has been constructed with the features of FIGS. 1-12. The light-emitting smell-altering aroma dispenser functions smoothly to provide all of the features disclosed earlier.

Although particular embodiments of the invention have been described in detail for purposes of illustration, various modifications and enhancements may be made without departing from the spirit and scope of the invention. Accordingly, the invention is not to be limited except as by the appended claims.

What the invention claimed is:

1. A light-emitting smell-altering aroma dispenser, comprising:

a casing, said casing having a top wall, a peripheral wall, a bottom wall, an accommodation chamber, a plurality of through holes located on said top wall, a wire hole located on said peripheral wall at one side, and an opening located on said bottom wall;

a plurality of heater members mounted in said accommodation chamber and respectively aimed at said through holes, each said heater member having an axial center through hole;

a plurality of trays respectively arranged at a bottom side of said heater members, each said tray having a tray body shaped like a hollow rounded dish, a tubular stem located on a bottom side of said tray body and at least one leg;

a base member affixed to said casing to close said opening;

a control circuit board fastened to the legs of said trays and adapted for providing electricity to said heater members to generate heat subject to a predetermined operation mode, said control circuit board comprising a power jack positioned in said wire hole of said casing for the connection of an external power cord;

a plurality of aroma containers respectively inserted through the through holes of said casing and the axial center through holes of said heater members and supported on said trays and kept in close contact with the periphery of the axial center through hole of the associating heater member for holding at least one aromatic substance that releases a smell when heated a plurality of light emitting devices mounted in the tubular stems of said trays and controllable by said control circuit board to emit light toward said aroma containers.

2. The light-emitting smell-altering aroma dispenser as claimed in claim 1, wherein the number of said aroma containers is 2; the number of said through holes is 2; the number of said heater members is 2; the number of said trays is 2; the number of said light emitting devices is 2, and the two light emitting devices are respectively mounted in the tubular stems of the two trays.

3. The light-emitting smell-altering aroma dispenser as claimed in claim 1, wherein each said aroma container has a respective aromatic substance contained therein.

4. The light-emitting smell-altering aroma dispenser as claimed in claim 3, wherein the aromatic substance contained in each said aroma container is selected from a group of essential oil, scented candle, flower essence and fragrance and prepared in a predetermined color.

5. The light-emitting smell-altering aroma dispenser as claimed in claim 1, wherein said heater members are prepared from one of a group of mica, PTC (positive temperature coefficient technology) resistor and cement resistor.

6. The light-emitting smell-altering aroma dispenser as claimed in claim 1, wherein said casing has a plurality of locating holes located on the bottom wall thereof, and a plurality of clamping plates respectively fastened to said locating holes; said base member has a plurality of mounting notches that are respectively fastened to said clamping plates when said base member is fastened to said casing to close said opening.

7. The light-emitting smell-altering aroma dispenser as claimed in claim 1, wherein the number of said aroma containers is 3; the number of said through holes is 3; the number of said heater members is 3; the number of said trays is 3; the number of said light emitting devices is 3, and the three light emitting devices are respectively mounted in the tubular stems of the three trays.

8. The light-emitting smell-altering aroma dispenser as claimed in claim 1, wherein each said aroma container has a top opening sealed with a plug, said plug having ribs extending around the periphery thereof for friction engagement with the periphery of the top opening of one said aroma container.

9. The light-emitting smell-altering aroma dispenser as claimed in claim 1, wherein said control circuit board has at least one light emitting device installed therein; said casing admits light from the at least one light emitting device at said control circuit board.

10. A light-emitting smell-altering aroma dispenser, comprising:

a casing, said casing having a top wall, a peripheral wall, a bottom wall, an accommodation chamber, a through hole located on said top wall, a wire hole located on said peripheral wall at one side, and an opening located on said bottom wall;

at least one heater member mounted in said accommodation chamber of said casing and aimed at said through hole, each said heater member having an axial center through hole;

at least one tray arranged at a bottom side of said at least one heater member, each said tray having a tray body shaped like a hollow rounded dish, a tubular stem located on a bottom side of said tray body and at least one leg;

a base member affixed to said casing to close said opening;

at least one aroma container inserted through the through hole of said casing and the axial center through hole of each said heater member and supported on said at least one tray and kept in close contact with the periphery of the axial center through hole of each said heater member for holding at least one aromatic substance that releases a smell when heated by said at least one heater member upon connection of electricity to said at least one heater member; and at least one light emitting device installed in the tubular stem of said at least one tray and controllable to emit light toward said at least one aroma container.

11. The light-emitting smell-altering aroma dispenser as claimed in claim 10, further comprising a control circuit board fastened to the leg of said at least one tray and adapted for providing electricity to said at least one heater member to generate heat subject to a predetermined operation mode, said control circuit board comprising a power jack positioned in said wire hole of said casing for the connection of an external power cord.

12. The light-emitting smell-altering aroma dispenser as claimed in claim 10, wherein each said aroma container has a respective aromatic substance contained therein.

13. The light-emitting smell-altering aroma dispenser as claimed in claim 12, wherein the aromatic substance contained in each said aroma container is selected from a group of essential oil, scented candle, flower essence and fragrance and prepared in a predetermined color.

14. The light-emitting smell-altering aroma dispenser as claimed in claim 11, wherein said control circuit board has at least one light emitting device installed therein; said casing admits light from the at least one light emitting device at said control circuit board.

15. The light-emitting smell-altering aroma dispenser as claimed in claim 10, wherein each said heater member is prepared from one of a group of mica, PTC (positive temperature coefficient technology) resistor and cement resistor.

16. The light-emitting smell-altering aroma dispenser as claimed in claim 10, wherein said base member has a plurality of columns; each said heater member has a plurality of lugs respectively affixed to said columns of said base member.

17. The light-emitting smell-altering aroma dispenser as claimed in claim 10, wherein each said aroma container has a top opening sealed with a plug, said plug having ribs extending around the periphery thereof for friction engagement with the periphery of the top opening of one said aroma container.

* * * * *